United States Patent
Vandewalle (10) Patent No.: US 7,338,493 B1
(45) Date of Patent: Mar. 4, 2008

(54) METHOD AND APPARATUS FOR CEMENTING A SCREW ANCHOR

(75) Inventor: Mark V Vandewalle, Pierceton, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 616 days.

(21) Appl. No.: 10/608,701

(22) Filed: Jun. 27, 2003

Related U.S. Application Data (60) Provisional application No. 60/392,492, filed on Jun. 28, 2002.

(51) Int. Cl.
A61B 17/56 (2006.01)

(52) U.S. Cl. ........................................................ 606/73
(58) Field of Classification Search ................... 606/65, 606/69–73, 92–94, 104; 623/17.11–17.16
See application file for complete search history.

(56) References Cited

U.S. PATENT DOCUMENTS

| | | | |
|---|---|---|---|
| 126,366 A | 4/1872 | Wills | |
| 837,767 A | 12/1906 | Aims | |
| 2,242,003 A | 5/1941 | Lorenzo | |
| 2,526,959 A | 10/1950 | Lorenzo | |
| 3,051,169 A | 8/1962 | Grath | |
| 3,240,379 A | 3/1966 | Bremer et al. | |
| 3,379,019 A | 4/1968 | Williams | |
| 3,897,713 A | 8/1975 | Gugle | |
| 3,907,442 A | 9/1975 | Reid | |
| 3,987,499 A | 10/1976 | Scharbach et al. | |
| 4,044,512 A | 8/1977 | Fischer et al. | |
| 4,065,817 A | 1/1978 | Branemark et al. | |
| 4,098,166 A | 7/1978 | Lang | |
| 4,431,416 A | 2/1984 | Niznick | |
| 4,488,875 A | 12/1984 | Niznick | |
| 4,494,535 A | 1/1985 | Haig | |
| 4,645,453 A | 2/1987 | Niznick | |
| 4,653,487 A | 3/1987 | Maale | |
| 4,653,489 A | 3/1987 | Tronzo | |
| 4,712,957 A | 12/1987 | Edwards et al. | |

(Continued)

FOREIGN PATENT DOCUMENTS

EP 0 490 417 A1 6/1992

(Continued)

Primary Examiner—Eduardo C. Robert
Assistant Examiner—Michael J Araj
(74) Attorney, Agent, or Firm—Harness, Dickey & Pierce, P.L.C.

(57) ABSTRACT

A bone screw anchor capable of securely fastening a fixation device to weak or brittle bone. The anchor includes a distal region terminating in an open aperture or a solid tapered terminus. The distal region may include cutting flutes and a helical thread extending through an intermediate region, so as to make the anchor self-cutting. The proximal region has a receptor for receiving a driver for driving the anchor within a bore or hole within the bone. The anchor has an interior bore with internal threads for receiving a bone screw used to secure a fixation device to the anchor. The bore may have a plurality of ports providing passage to the exterior of the anchor. Once seated entirely within the receptor, the anchor's position is secured using bone cement. Bone cement is delivered to the bore or hole before the anchor is placed in the receptor or after via the ports.

33 Claims, 6 Drawing Sheets

U.S. PATENT DOCUMENTS

| | | |
|---|---|---|
| 4,758,161 A | 7/1988 | Niznick |
| 4,760,844 A | 8/1988 | Kyle |
| 4,772,261 A | 9/1988 | Von Hoff et al. |
| 4,787,882 A | 11/1988 | Clarén |
| 4,790,297 A | 12/1988 | Luque |
| 4,860,513 A | 8/1989 | Whitman |
| 4,893,974 A | 1/1990 | Fischer et al. |
| 4,960,381 A | 10/1990 | Niznick |
| 4,993,900 A | 2/1991 | Hügel et al. |
| 5,030,095 A | 7/1991 | Niznick |
| 5,047,030 A | 9/1991 | Draenert |
| 5,061,181 A | 10/1991 | Niznick |
| 5,062,800 A | 11/1991 | Niznick |
| 5,071,350 A | 12/1991 | Niznick |
| 5,076,788 A | 12/1991 | Niznick |
| RE33,796 E | 1/1992 | Niznick |
| 5,078,607 A | 1/1992 | Niznick |
| 5,098,435 A | 3/1992 | Stednitz et al. |
| 5,129,901 A | 7/1992 | Decoste |
| 5,143,498 A | 9/1992 | Whitman |
| 5,145,301 A | 9/1992 | Yamamoto |
| 5,192,282 A | 3/1993 | Draenert |
| 5,209,805 A | 5/1993 | Spraggins |
| 5,214,987 A | 6/1993 | Fenton, Sr. |
| 5,249,899 A | 10/1993 | Wilson |
| 5,253,965 A | 10/1993 | Angel |
| 5,281,140 A | 1/1994 | Niznick |
| 5,334,024 A | 8/1994 | Niznick |
| 5,338,197 A | 8/1994 | Kwan |
| 5,427,527 A | 6/1995 | Niznick et al. |
| 5,433,606 A | 7/1995 | Niznick et al. |
| 5,483,781 A | 1/1996 | Ernst et al. |
| 5,484,442 A | 1/1996 | Melker et al. |
| 5,531,748 A | 7/1996 | de la Caffiniere |
| 5,545,228 A | 8/1996 | Kambin |
| 5,569,251 A * | 10/1996 | Baker et al. .................. 606/69 |
| 5,571,017 A | 11/1996 | Niznick |
| 5,575,650 A | 11/1996 | Niznick et al. |
| 5,580,352 A | 12/1996 | Sekel |
| 5,593,407 A | 1/1997 | Reis |
| 5,601,559 A | 2/1997 | Melker et al. |
| 5,622,500 A | 4/1997 | Niznick |
| 5,628,752 A | 5/1997 | Asnis et al. |
| 5,665,087 A | 9/1997 | Huebner |
| 5,725,581 A | 3/1998 | Branemark |
| 5,733,083 A | 3/1998 | Heminger |
| 5,743,912 A | 4/1998 | Lahille et al. |
| 5,788,702 A | 8/1998 | Draenert |
| 5,800,407 A | 9/1998 | Eldor |
| 5,871,484 A | 2/1999 | Spievack et al. |
| 5,885,041 A | 3/1999 | Giannuzzi et al. |
| 5,885,079 A | 3/1999 | Niznick |
| 5,893,850 A | 4/1999 | Cachia |
| 5,941,911 A | 8/1999 | Buechel |
| 5,989,028 A | 11/1999 | Niznick |
| 6,004,327 A | 12/1999 | Asnis et al. |
| 6,048,204 A | 4/2000 | Klardie et al. |
| 6,048,343 A | 4/2000 | Mathis et al. |
| 6,210,376 B1 | 4/2001 | Grayson |
| 6,214,012 B1 | 4/2001 | Karpman et al. |
| 6,240,696 B1 | 6/2001 | Ludwig et al. |
| 6,244,867 B1 | 6/2001 | Aravena et al. |
| 6,287,117 B1 | 9/2001 | Niznick |
| 6,517,579 B1 * | 2/2003 | Paulos et al. ............ 623/13.14 |
| 6,613,053 B1 * | 9/2003 | Collins et al. ................ 606/69 |
| 6,629,977 B1 * | 10/2003 | Wolf ........................... 606/73 |
| 6,755,835 B2 * | 6/2004 | Schultheiss et al. .......... 606/73 |
| 2001/0021852 A1 | 9/2001 | Chappius |
| 2002/0042615 A1 * | 4/2002 | Graf et al. .................... 606/73 |
| 2003/0191530 A1 * | 10/2003 | Sklar ....................... 623/13.14 |

FOREIGN PATENT DOCUMENTS

| | | | |
|---|---|---|---|
| JP | 7-51292 | 2/1995 | |
| JP | 10-211213 | 8/1998 | |
| WO | WO 01/12088 A1 * | 2/2001 | .................. 606/73 |

* cited by examiner

METHOD AND APPARATUS FOR CEMENTING A SCREW ANCHOR

CROSS-REFERENCE TO RELATED APPLICATIONS

This application claims the benefit of U.S. Provisional Application No. 60/392,492, filed on Jun. 28, 2002. The disclosure of the above application is incorporated herein by reference.

FIELD OF THE INVENTION

The present invention relates to surgical applications for the repair of bone fractures and deformities. More particularly, the present invention relates to a method and apparatus for anchoring a bone fixation device to an exterior bone surface.

BACKGROUND OF THE INVENTION

It is well known in the art to use fixation devices to aid in the repair of bone defects such as bone fractures. Fixation devices are available in a wide variety of different shapes and sizes, such as a rigid plate. After the defective bone is set in proper position by a physician, the fixation device is used to secure the bone in this position during the healing process. Preferably, the fixation device is placed over the defective portion of the bone and anchored to the bone using any suitable fastening device, such as a bone screw.

While current fastening devices are capable of securing fixation devices to bone that is strong and healthy, current fastening devices fail when the bone is weak and brittle, as is often found in the elderly. Weak and brittle bone severely hampers fastener purchase and often results in the fastener becoming dislodged from the bone. Consequently, there is a need for a fastening device or system that is capable of securely fastening a fixation device to bone that is weak or brittle.

SUMMARY OF THE INVENTION

The present invention provides for a bone screw anchor that is capable of securely fastening a fixation device to bone that is weak or brittle. The fastening device includes a distal region that may terminate in an open aperture or a solid tapered terminus. The distal region may include a plurality of cutting flutes and an elongated helical thread extending through an intermediate region, so as to provide a self cutting anchor. The proximal region has a receptor for receiving a driver so as to aid in the driving of the anchor directly within the bone or within a pre-drilled, elongated bore within the bone.

The anchor further has an interior bore with internal threads. The bore may have a plurality of ports providing passage from the bore to the exterior of the anchor. After the anchor is driven entirely within the elongated bore, its position is secured using bone cement. The bone cement may be delivered to the elongated bore before the anchor is placed in the bore or via the ports after it is seated. Once the bone cement has hardened so as to secure the anchor within the weak or brittle bone, a suitable fixation device may be secured to the anchor using a suitable bone screw, the bone screw being coupled to the anchor via the internal threads.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
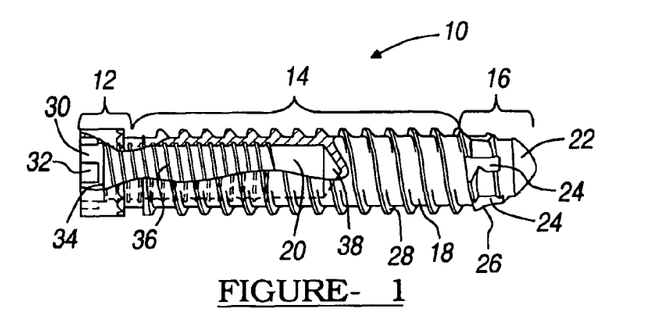
FIG. 1 is a partially sectioned side view of a screw anchor of the present invention.

Referring to FIG. 1, a bone screw anchor according to a first preferred embodiment of the present invention is generally identified at reference numeral 10. The bone screw anchor 10 generally has a proximal region 12 (FIG. 1A), an intermediate region 14, and a distal region 16. Further, the anchor 10 has an exterior surface 18 and an interior bore 20.

The anchor 10 is generally cylindrically shaped and is of a suitable length so as to securely engage a bone as further discussed herein.

The distal region 16 is comprised of a tapered terminus 22 and a plurality of cutting flutes 24 extending from exterior surface 18. The cutting flutes 24 each contain at least one tooth 26. Running through and extending from the cutting flutes 24 is an external bone engaging helical thread 28. The helical thread 28 extends along the exterior surface 18 from the distal region 16 and spans the length of the intermediate region 14. Tapered terminus 22, flutes 24, and helical thread 28 allow the anchor 10 to be self-cutting. This enables the anchor 10 to either be driven directly into a bone or into a pre-drilled bore formed within the bone, eventhough it is contemplated that in most instances the anchor 10 will be implanted within a drilled bone or into a pre-tapped bore formed within the bone.

Figure 1A:
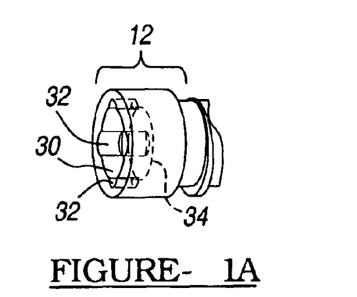
FIG. 1A is a three-quarter, partially sectioned, side perspective view of the proximal portion of the screw anchor of FIG. 1.

Formed within the proximal region 12 is a receptor 30. The receptor 30 has at least one niche or groove 32 for receiving a corresponding projection of a suitable driving tool. The receptor 30 takes the place of a head and allows the anchor 10 to be driven completely within a bone so that no portion of the anchor 10 extends from the bone. The receptor 30 contains an opening 34 to provide access to the interior bore 20.

The bore 20 preferably extends from opening 34 to approximately a mid-point of the intermediate region 14, however, the depth of the bore 20 may vary. The interior bore 20 contains a helical machine thread 36 capable of cooperating with threads of a suitable fastener. The helical machine thread 36 extends from the proximal region 12 to a desired point within the intermediate region 14. It is not necessary that the helical thread 36 extend the entire length of the bore 20. The bore 20 terminates in a conical shaped region 38.

Anchor 10 may be manufactured using any suitable biocompatible material such as, but not limited to, stainless steel, polyethylene, titanium, and cobalt chrome molybdenum. Regardless of the material used, it is preferred that the material be sufficiently rigid to allow the anchor to be self-cutting and should be compatible with the particular device secured using anchor 10, however, this may not be necessary in all applications. Preferably, anchor 10 and the secured device are of the same material. The anchor 10 may also be formed of a suitable resorbable material as well. Should the anchor 10 be formed of a material that is not sufficiently rigid for self-cutting, the bone may be tapped before insertion of the anchor 10.

The configuration and composition of anchor 10 allows anchor 10 to cut and rigidly engage a variety of different bones and bone regions. For example, anchor 10 is suitable for penetrating and securely engaging both cortical and cancellous regions of the femur bone or any other appropriate bone.

Figure 2:
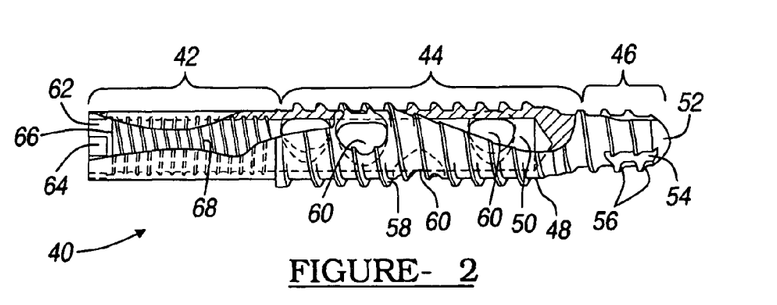
FIG. 2 is a partially sectioned side view of a screw anchor according to a second embodiment of the present invention.

A screw anchor according to a second preferred embodiment of the present invention is illustrated at FIG. 2 at reference numeral 40. Similar to bone anchor 10 of the first preferred embodiment, bone anchor 40 has a proximal region 42, an intermediate region 44, and a distal region 46. The anchor 40 also has an exterior surface 48 and an interior bore 50. The anchor 40 is generally cylindrically shaped and is of a suitable length so that it may be placed within a bone to a depth so as to adequately secure the anchor 40 in the bone.

The distal region 46 comprises a tapered terminus 52 and a plurality of elongated cutting flutes 54 extending from the exterior surface 48. The distal region 46 is similar to the distal region 16 of anchor 10 except that distal region 46 is substantially longer. Further, cutting flutes 54 are similar to cutting flutes 24 of anchor 10, except that flutes 54 are elongated and contain multiple teeth 56.

Running through and extending from the cutting flutes 54 is an external helical thread 58. The helical thread 58 extends along the exterior surface 48 from the distal region 46 and spans the entire length of the intermediate region 44. Tapered terminus 52, flutes 54, and helical thread 58 allow the anchor 40 to be self-cutting and/or self-tapping, eventhough the anchor 40 is most commonly implanted in a pre-tapped bone.

The intermediate region 44 contains a plurality of ports 60. The ports 60 may be placed at any location within the intermediate region 44 but are preferably placed in a staggered configuration at 120° intervals, as seen in FIG. 2. The ports extend from the interior bore 50 to the exterior surface 48 and allow for the passage of material, such as bone cement, from the interior bore 50 to the exterior surface 48. Obviously, the helical thread 58 is interrupted by the presence of ports 60.

Formed within proximal region 42 is a receptor 62. The receptor 62 has at least one niche or groove 64 for receiving a corresponding projection of a suitable driving tool. The receptor 62 takes the place of a head and allows the anchor 40 to be driven completely within a bone so that no portion of the anchor 40 extends from the bone. The receptor 62 contains an opening 66 to provide access to the interior bore 50.

The interior bore 50 extends from opening 62 through the entire length of the proximal region 42 and preferably extends the entire length of the intermediate region 44. While the length of the interior bore 50 may vary, the bore 50 should at least extend beyond each of the ports 60. Within the bore 50 is a helical machine thread 68 that is capable of cooperating with threads of a suitable fastener. The bore 50 preferably extends through the entire length of the proximal region 42, but may also extend to any point within the intermediate portion 44.

Like anchor 10 of the first embodiment, anchor 40 may be manufactured using any suitable biocompatible material such as, but not limited to, stainless steel, polyethylene, titanium, and cobalt chrome molybdenum. Regardless of the material used, it is preferred that the material be sufficiently rigid to allow the anchor to be self-cutting and should be compatible with the particular device secured using anchor 40, however, this may not be necessary in all applications. Preferably, anchor 40 and the secured device are of the same material.

Also similar to anchor 10, the configuration and composition of anchor 40 allows it to cut and rigidly engage a variety of different bones and bone regions. For example, anchor 40 is suitable for penetrating and securely engaging both cortical and cancellous regions of the femur bone or any other appropriate bone.

Figure 3A:
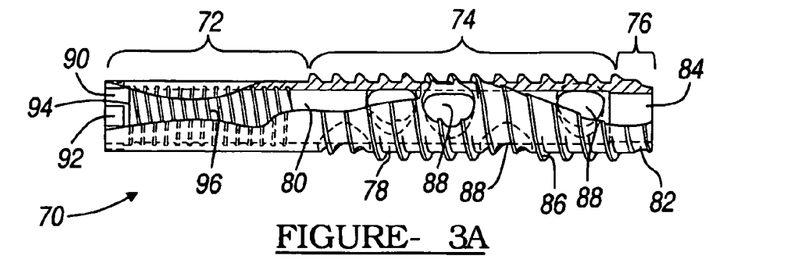
FIG. 3A is a partially sectioned side view of a screw anchor according to a third embodiment of the present invention.

A screw anchor according to a third preferred embodiment of the present invention is illustrated at FIG. 3A at reference numeral 70. Similar to bone anchor 10 and bone anchor 40 described above, bone anchor 70 has a proximal region 72, an intermediate region 74, and a distal region 76. The anchor 70 also has an exterior surface 78 and an interior bore 80. The anchor 70 is generally cylindrically shaped and is of a suitable length so that it may be placed within a bone to a depth so as to adequately secure the anchor in the bone.

The distal region 76 has a tapered terminus 82 with an aperture 84. Aperture 84 allows for communication between bore 80 and the exterior 78 of anchor 70. Thus, unlike the above described embodiments the bore 80 extends the entire length of the anchor 70 from the distal region 76 to the proximal region 72.

Extending from the distal region 76 is a helical thread 86. The helical thread 86 extends along the exterior surface 78 from the distal region 76 and spans the entire length of the intermediate region 74. The presence and configuration of helical thread 86 allows anchor 70 to be self-cutting and/or self-tapping, eventhough the anchor 70 will commonly be implanted within a pre-cut and/or pre-tapped bone.

Similar to anchor 40 of the second embodiment, the intermediate region 74 of anchor 70 contains a plurality of ports 88. The ports 88 may be placed at any location within the intermediate region 74 but are preferably placed in a staggered configuration at 120° intervals throughout the intermediate region 74, as seen in FIG. 3. The ports 88 extend from the exterior surface 78 to the interior bore 80 and allow for the passage of material, such as bone cement, from the interior bore 80 to the exterior surface 78. The presence of ports 88 interrupts helical thread 86.

Formed within the proximal region 72 is a receptor 90. The receptor 90 has at least one niche or groove 92 for receiving a corresponding projection of a suitable driving tool. The receptor 90 takes the place of a head and allows the anchor 70 to be driven completely within the bone so that no portion of the anchor 70 extends from the bone. The receptor 90 contains an opening 94 to provide access to the interior bore 80.

As discussed above, interior bore 80 extends the entire length of the anchor 70. The interior bore 80 contains a helical thread 96 capable of receiving a suitable fastener. The helical thread 96 preferably extends the entire length of the proximal region 72, but may extend for only a portion of the proximal region 72 or may also extend into the intermediate region 74.

Like the above described embodiments, anchor 70 may be manufactured using any suitable biocompatible material such as, but not limited to, stainless steel, polyethylene, titanium, and cobalt chrome molybdenum. Regardless of the material used, it is preferred that the material be sufficiently rigid to allow the anchor to be self-cutting and should be compatible with the particular device secured using anchor 70, however, this may not be necessary in all applications. Preferably, anchor 70 and the fixation device are of the same material.

Anchor 70 is also similar to the above described embodiments in that its configuration and composition allow it to cut and rigidly engage a variety of different bones and bone regions. For example, anchor 70 is suitable for penetrating and securely engaging cancellous bone regions. However, unlike the above described embodiments, anchor 70 is unable to be driven within cortical bone regions as the distal region 76 is open due to the presence of aperture 84. Further, the absence of a tapered terminus at the distal region 76 hampers the ability of anchor 70 to be driven within cortical bone without initial pre-drilling and tapping of the bone.

Figure 3B:
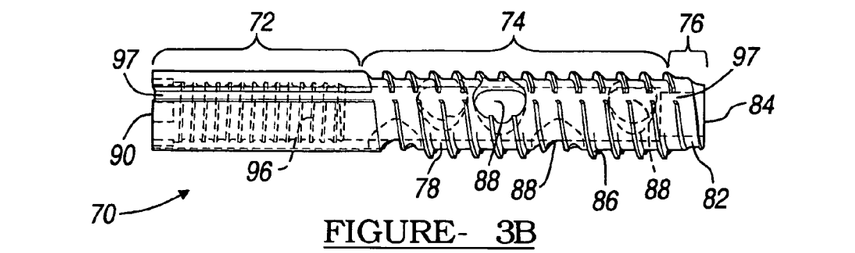
FIG. 3B is a side view of the screw anchor of FIG. 3A further comprising a flute.

As seen in FIG. 3B, anchor 70 may optionally include at least one flute 97. The flutes 97 preferably extend approximately the entire length of the intermediate region 74 and approximately the entire length of the proximal region 72. Within the intermediate region 74 the flutes 97 are preferably formed as interruptions within helical thread 86. Preferably, the flutes 97 do not extend within exterior surface 78, however, flutes 97 may extend within exterior surface 78 in some applications. Within the proximal region 72 flutes 97 are preferably formed within the exterior surface 78 to a depth that is approximately equal to the depth of helical thread 86. Thus, in order to accommodate flutes 97 the proximal region 72 is preferably raised to a height approximating the height of helical thread 86 as seen in FIG. 3B. While the number and location of flutes 97 may vary, it is preferred that the number of flutes 97 is sufficient such that all ports 88 communicate with a flute 97. Thus, because the ports 88 are preferably spaced at 120° intervals along the exterior 78 of anchor 70, flutes 97 are also preferably placed at 120° intervals. While flutes 97 are described and illustrated in conjunction with anchor 70, it must be noted that the flutes 97 may also be used in conjunction with anchor 10 and anchor 40.

Figure 3C:
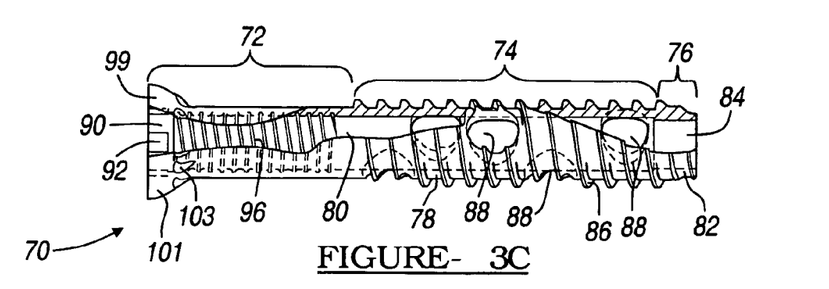
FIG. 3C is a partially sectioned side view of the screw anchor of FIG. 3A further comprising a collar.
Figure 3D:
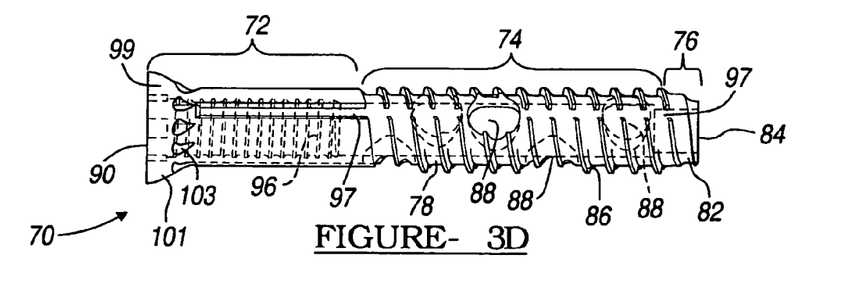
FIG. 3D is a side view of the screw anchor of FIG. 3A further comprising a collar and flute.

As seen in FIG. 3C, anchor 70 may also include a collar 99. Collar 99 is preferably integral to anchor 70 and located upon the exterior surface 78 of receptor 90. The collar 99 may be of any suitable shape but preferably extends linearly from receptor 90 and is conically tapered towards intermediate region 74. A bottom surface 101 of collar 99 contains at least one cutting flute 103 so as to permit the collar 99 to be driven within the bone. While collar 99 is generally illustrated and described in association with anchor 70, it must be realized that collar 99 may be used in conjunction with any of the above described anchors. Further, it must be realized that anchor 70 may be outfitted with both collar 99 and flutes 97.

With reference to FIGS. 4 through 11, the installation and operation of anchor 70 is described below. As the installation and operation of anchor 70 is substantially similar to anchor 40 and anchor 10, a detailed description of anchors 40 and 10 is not necessary. Any differences between the installation and operation of anchors 10, 40, and 70 are fully described below.

Figure 4:
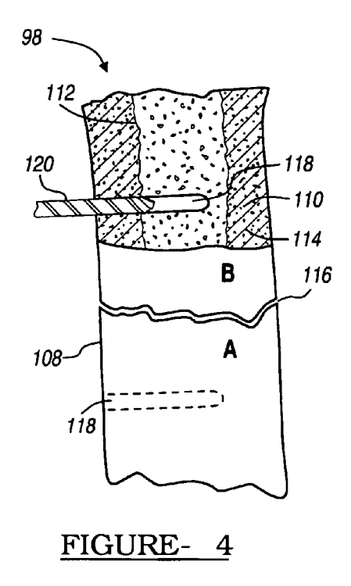
FIG. 4 is a partially sectioned side view of a fractured bone, the bone having two bores or holes formed by the illustrated drill bit.

FIG. 4 generally illustrates a bone 98. The bone 98 generally includes an outer surface 108 and an inner region 110. The inner region 110 includes numerous different composition regions and layers but is generally comprised of a spongy cancellous region 112 surrounded by a hard cortical region 114.

As illustrated, the bone 98 contains a bone defect at fracture point 116, causing the bone 98 to be severed into two halves A and B. It must be noted that the bone defect may be any type of defect and may be present in numerous different bones of the body. Thus, bone 98 and fracture 116 are shown for illustrative purposes only.

The severed halves A and B of the bone 98 have been realigned by a physician to their natural position. To insure that the severed halves A and B heal in their natural relationship to each other, they may be affixed in the position set by the physician prior to healing. To aid in the affixation of severed half A to severed half B, elongated bores or holes 118 are formed within the bone 98. The bores or holes 118 are used to secure a fixation device to the bone 98 so as to secure the bone 98 in the pre-set position. While the two bores or holes 118 are illustrated as being located on either side of fracture 116, the number and position of bores or holes 118 may vary according to physician preference, according to the type of defect being treated, and according to the particular device to be secured using anchor 70. The bores or holes 118 may be formed in any suitable manner such as through the use of a drill bit 120 connected to a drill (not shown). The bores or holes 118 may extend to any suitable depth within the bone 98, but preferably extend through the cortical bone 114 and terminate within the cancellous bone 112 as shown in FIG. 4.

Figure 5:
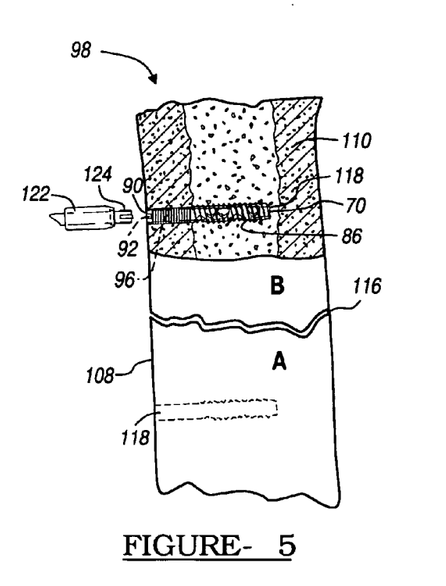
FIG. 5 is a partially sectioned side view of the bone of FIG. 4 with the screw anchor of FIG. 3A seated within the bore, the screw anchor having been driven within the bore using the illustrated driver.

As illustrated in FIG. 5, after bores or holes 118 are formed within the bone 98, anchor 70 is inserted within the bores or holes 118. As described above, anchor 70 is self-cutting and self-tapping and may be easily inserted into bore or hole 118 using a suitable insertion device, such as driver 122. Driver 122 engages anchor 70 through cooperation between teeth 124 of the driver 122 and niches or grooves 92 of receptor 90. Once driver 122 engages anchor 70, the driver 122 is used to drive the anchor 70 within the bone 98 at an orientation that is approximately perpendicular to the bone surface 108. As the anchor 70 is driven within the bone 98, the anchor 70 is also rotated so that the helical thread 86 engages bores or holes 118, thus securing the anchor 70 within the bone 98. The anchor 70 may be inserted within the bore or hole 118 to any suitable depth, but is at least inserted to a depth such that that the entire anchor 70 is fully within the bone 98.

Weak or brittle bone 98 negatively affects fastener purchase and may cause the helical thread 86 to lose its grip within the bore or hole 118, thus causing the anchor to become dislodged from the bone 98. In order to secure the anchor 70 within bone 98 that is weak and brittle, bone cement 126 may be inserted into the bore or hole 118.

Figure 6:
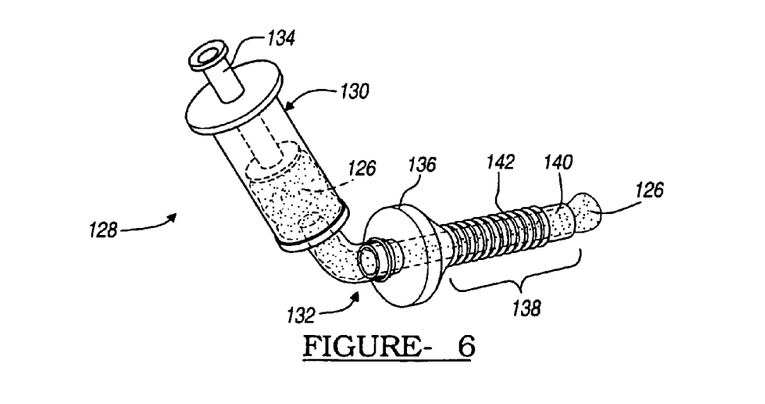
FIG. 6 is a perspective view of a cement delivery apparatus.

Bone cement 126 may be inserted into the bores or holes 118 using any suitable device such as a cement delivery apparatus 128. As illustrated in FIG. 6, delivery apparatus 128 is generally comprised of a bone cement receptacle 130 and a delivery tube 132. Cement receptacle 130 simply retains the bone cement 126 until delivery to the bore or hole 118 is desired. When delivery is desired, the cement 126 is displaced from receptacle 130 and forced through the delivery tube 132 using plunger 134.

Figure 7:
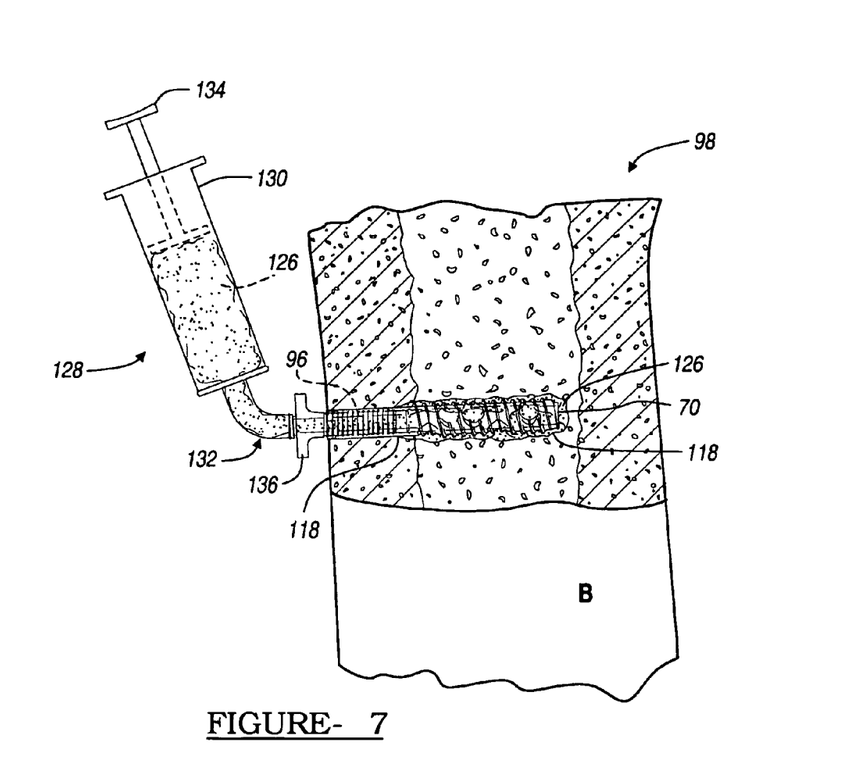
FIG. 7 is a partially sectioned side view of the bone of FIG. 4 illustrating the use of the cement delivery apparatus of FIG. 6 to introduce bone cement to the bore via the anchor.

The delivery tube 132 is comprised of a head 136 and an elongated tube 138. As seen in FIG. 7, the head 136 cooperates with receptor 90 and prevents the delivery tube 132 from being inserted within the bore 80 beyond a desirable depth. The elongated tube 138 has an exterior surface 140 with a helical thread 142. The helical thread 142 cooperates with internal thread 96 so as to both secure the delivery tube 132 within the bore 80 and to make sure that no bone cement 126 becomes clogged within internal threads 96.

Figure 8:
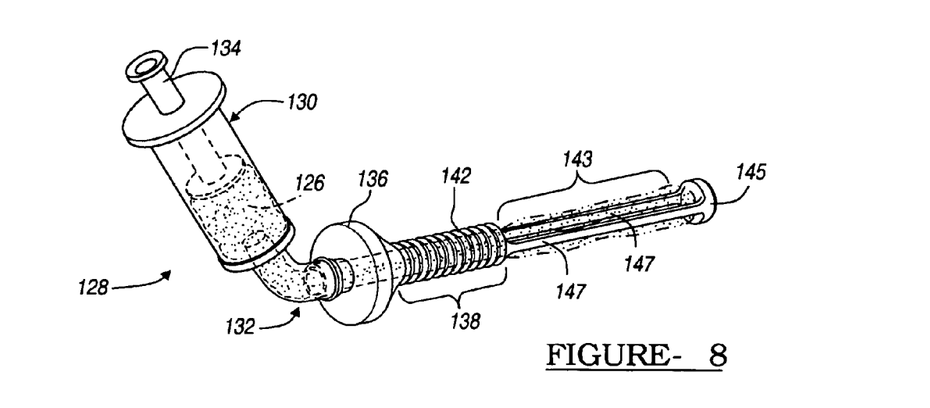
FIG. 8 is a perspective view of the cement delivery apparatus having a disk supported by a stem.

As illustrated in FIG. 8, delivery apparatus 128 may be configured to include a stem 143 and a disk 145. Stem 143 extends from elongated tube 138 and preferably takes the form of two elongated supports 147. The supports 147 are of a suitable length so as to extend approximately the entire length of intermediate region 74 and support disk 145 within aperture 84. The size of disk 145 closely approximates the size of aperture 84. Thus, when disk 145 is seated within aperture 84 the disk 145 seals aperture 84 and prevents bone cement 126 from exiting aperture 84. Delivery apparatus 128 having elongated supports 147 and disk 145 is used when the introduction of bone cement to hole 118 via aperture 84 is not desired.

The use of delivery apparatus 128 with disk 145 supported by stem 143 is advantageous as it allows anchor 10 and anchor 40 to be manufactured with an open distal region 22, 46 so that the anchors 10, 40 may be used in situations where it is desirable to use an anchor with an open distal region 22, 46 but where it is undesirable to introduce cement at the end of bore or hole 118. Thus, the use of delivery apparatus 128 having disk 145 supported by stem 143 provides anchors 10, 40 with added functionality.

In the event that the use of disk 145 as a seal is not desirable, the disk 145 may be removed by severing stem 143 using a suitable severing device. In order to facilitate the severing of stem 143, the stem 143 may be provided with a pre-notch or weakened portion (not specifically shown). Further, stem 143 and disk 145 may be produced in a variety of different shapes and sizes so that they may be used with a variety of different anchors. As the delivery apparatus 128 configured with stem 143 and disk 145 may be used with a variety of different anchors and in a variety of different situations, its use is advantageous as it reduces inventory levels.

Figures 9, 10:
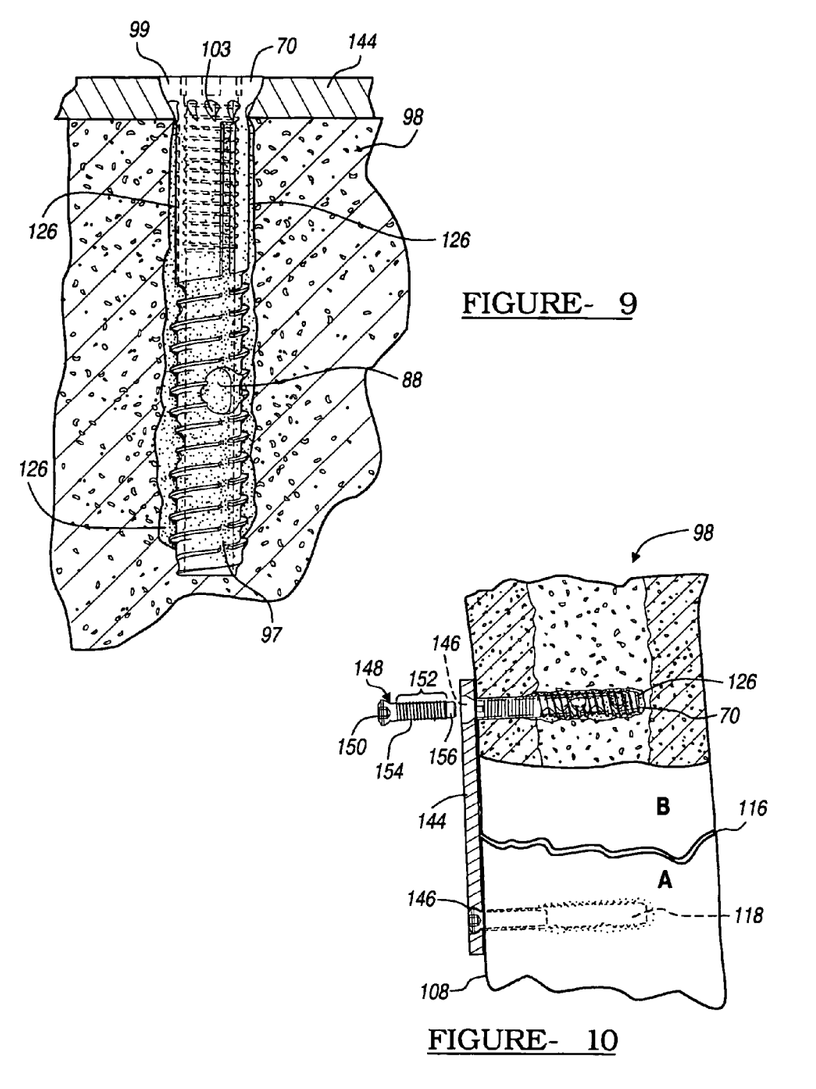
FIG. 9 is a sectional side view of the bone of FIG. 4 showing the anchor of FIG. 3D secured within the bone by bone cement.
FIG. 10 is a partially sectioned side view of the bone of FIG. 4 illustrating the fastening of a fixation plate to an exterior portion of the bone through the cooperation of a bone screw and the screw anchor of FIG. 3A.

Bone cement 126 delivered to internal bore 80 exits internal bore 80 through ports 88 and aperture 84 so as to fill the bore or hole 118 and adjoining bone interstices (FIG. 7). As seen in FIG. 9, when anchor 70 is provided with flutes 97, bone cement 126 travels through flutes 97 so as to better surround proximal region 72. To prevent the unlikely occurrence of bone cement 126 leaking from the hole 118 the anchor 70 may include collar 99. As seen in FIG. 9, when collar 99 is used the cement 126 directed towards the proximal region 72 is collected under collar 99 and prevented from exiting hole 118.

After the bone cement 126 hardens it provides a secure bond between anchor 70 and bore or hole 118. Consequently, anchor 70 is retained within the bone 98 even if the bone is weak and brittle. After bone cement 126 is delivered, the delivery tube 132 is removed from cooperation with helical thread 96 and removed from within the bore 80.

As illustrated in FIG. 10, after the bone cement 126 has hardened, a suitable fixation device, such as fixation plate 144, is placed upon the bone surface 108. While the fixation plate 144 is illustrated as a substantially planar plate having two apertures 146 at opposite ends of the plate 144, fixation plate 144 may be of any suitable size or shape and may include any suitable number of apertures 146, the apertures 146 being of any suitable size or configuration. The fixation plate 144 may be placed at any point on the bone 98 so as to hold bone 98 in the position previously set by a physician. However, the fixation plate 144 must be placed so that apertures 146 are aligned with anchors 70. Fixation plate 144 is preferably placed upon the bone 98 so that it spans the defect, illustrated as fracture 116 in FIG. 10.

Figure 11:
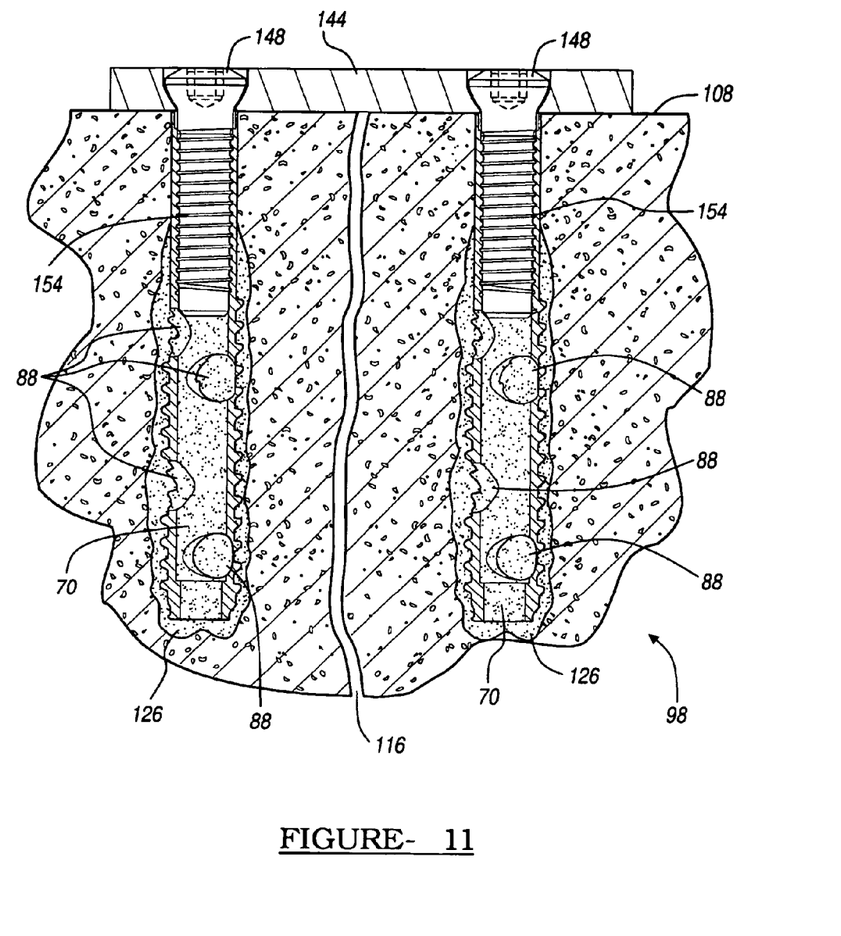
FIG. 11 is a sectional side view of the bone of FIG. 4 showing the fixation plate secured to the bone through cooperation between the bone screw and the screw anchor of FIG. 3A with the screw anchor secured within the elongated bores via bone cement.

Once the apertures 146 are aligned with anchors 70, the fixation plate 144 is secured to the anchors 70 using a suitable fastening device such as bone screw 148. Bone screw 148 may be any standard bone screw having a head 150, a threaded portion 152 with an elongated thread 154, and a tip portion 156. As seen in FIG. 10, the bone screw 148 is inserted through aperture 146 so that threads 154 cooperate with internal threads 96 of the anchor 70. The bone screw 148 is inserted to a depth so that the head 150 is fully seated within the fixation plate 144. It is this interaction between bone screw 148 and anchor 70, as seen in FIG. 11, that secures the bone screw 148 within the anchor 70 and consequently secures the fixation plate 144 to the bone 98.

Installation and operation of anchor 40 is substantially similar to the installation of anchor 70 described above. However, the presence of tapered terminus 52 prevents bone cement 126 from flowing out of the distal region 46 of the anchor 40. Further, the presence of tapered terminus 52 allows anchor 40 to be driven beyond bore or hole 118 and further into bone 98. Specifically, anchor 40 may be driven beyond the bore or hole 118 into hard cortical region 114. In contrast, due to the presence of aperture 84, anchor 70 does not have a piercing tip that would permit driving into the hard cortical region 114.

As described above, it is desirable to pre-drill bores or holes 118 into bone 98 before driving anchor 70 within bone 98. However, depending on the bone quality and the type and composition of the anchor used, it may be possible to simply drive the anchor within the bone without the need for pre-drilling the bone.

Installation and operation of anchor 10 is also very similar to the installation and operation of anchor 70. However, the delivery of bone cement through anchor 10 is not possible as anchor 10 does not have a bore or corresponding ports. Consequently, bone cement 126 must be delivered after the bore or hole 118 is drilled but before the anchor 10 is inserted within the bore or hole 118. While anchor 10 is self-cutting, the bore or hole 118 may be pre-tapped. The presence of tapered terminus 22 allows anchor 10, like anchor 70, to penetrate bone 98 beyond bore or hole 118 and into the cortical region 114. Finally, due to the absence of ports, anchor 10 has a an uninterrupted thread 28 that provides for greater purchase between anchor 10 and bone 98 as compared to anchor 40 and anchor 70.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A bone screw anchor system operable to secure an implant to a bone using a fastening device comprising:
   an intermediary portion having external threads;
   an open tip located proximate a first end of said intermediary portion;
   a head defining a groove capable of cooperating with a driving tool operable to facilitate implantation of said anchor within said bone, said head located proximate a second end of said intermediary portion opposite said open tip;
   a proximal portion between said head and said intermediary portion, said proximal portion is devoid of external threads, said proximal portion has a diameter that is at least approximately the same as a diameter of said external threads of said intermediary portion; and
   an interior bore extending through said head, through said proximal portion, and through said intermediary portion, said bore having threads at said proximal portion operable to cooperate with corresponding threads of the fastening device;
   wherein said fastening device secures the implant to the bone such that the implant is secured between the fastening device and the anchor.

2. The bone screw anchor system of claim 1, wherein said tip further comprises at least one cutting flute.

3. The bone screw anchor system of claim 1, wherein said tip is self-tapping.

4. The bone screw anchor system of claim 1, further comprising at least one port providing communication between said interior bore and an exterior of said bone screw anchor.

5. The bone screw anchor system of claim 1, further comprising at least one cutting flute extending across at least a portion of a length of said intermediary portion.

6. The bone screw anchor system of claim 1, wherein at least a portion of said bore is filled with bone cement.

7. The bone screw anchor system of claim 1, wherein said head further comprises a collar.

8. The bone screw anchor system of claim 7, wherein said collar further comprises at least one cutting flute.

9. The bone screw anchor system of claim 1, wherein said bore extends completely through said anchor.

10. The bone screw anchor system of claim 1, wherein said anchor is comprised of a resorbable material.

11. The bone screw anchor system of claim 1, wherein the implant is a bone plate.

12. The bone screw anchor system of claim 1, wherein said tip has a diameter that is smaller than a diameter of said intermediary portion.

13. The bone screw anchor system of claim 1, wherein said intermediary portion is completely externally threaded.

14. The bone screw anchor system of claim 1, wherein said fastening device is a screw.

15. The bone screw anchor system of claim 1, wherein said interface of said head is at least one recess operable to mate with said driver.

16. The bone screw anchor system of claim 1, wherein said intermediary portion further comprises a flute.

17. A bone screw anchor system operable to secure an implant to a bone using a fastening device comprising:
    an externally threaded intermediary portion;
    an open tip located proximate a first end of said intermediary portion;
    a head located proximate a second end of said intermediary portion, said second end positioned opposite said first end;
    a proximal region between said head and said intermediary portion, said proximal region is devoid of external threads; and
    a bore extending through said head, said intermediary portion, and said tip operable to direct bone cement from said bore to said bone through at least one of a port and said tip;
    wherein said bore includes internal threads confined to said proximal region for receiving the fastening device, which is operable to secure the implant to said anchor;
    wherein the implant is secured between the fastening device and the anchor.

18. The bone screw anchor system of claim 17, wherein said anchor is self tapping.

19. The bone screw anchor system of claim 17, further comprising at least one flute extending from said tip to said head.

20. The bone screw anchor system of claim 17, wherein said head further comprises a collar.

21. The bone screw anchor system of claim 17, wherein said collar further comprises at least one cutting flute.

22. The bone screw anchor system of claim 17, wherein said head further comprises an interface to permit cooperation between said anchor and a driving tool during implantation of said anchor within said bone.

23. The bone screw anchor system of claim 17, wherein said anchor is comprised of a resorbable material.

24. The bone screw anchor system of claim 17, wherein said bone cement is injected within said bore using a delivery apparatus comprising:
    a bone cement receptacle; and
    a threaded tube connected to said receptacle and operable to cooperate with said threads of said bore.

25. The bone screw anchor system of claim 24, said delivery apparatus further comprising a stem extending from said threaded tube, said stem terminating in a disk operable to plug said bore at said tip to prevent bone cement from passing through said tip.

26. The bone screw anchor system of claim 17, wherein said implant is a bone plate.

27. The bone screw anchor system of claim 17, wherein said tip has a diameter that is smaller than a diameter of said intermediary portion.

28. The bone screw anchor system of claim 17, wherein said intermediary portion is completely externally threaded.

29. The bone screw anchor system of claim 17, wherein said fastening device is a screw.

30. The bone screw anchor system of claim 17, wherein said interface of said head is at least one recess operable to mate with said driver.

31. The bone screw anchor system of claim 17, wherein said proximal region has a diameter that is at least approximately the same as a diameter of said externally threaded intermediary portion.

32. The bone screw anchor system of claim 31, wherein said proximal region further comprises a flute.

33. A method of securing a bone screw anchor system to a bone comprising:
- implanting a bone screw anchor within said bone using a driving tool operable to cooperate with a groove in a head of said anchor;
- injecting bone cement into an intermediate region of a bore extending through said anchor using a cement delivery device, said bone cement exiting said bore through at least one opening in the intermediate region to permit said bone cement to secure said anchor to said bone; and
- threading a fastening device into a threaded region of the bore to secure an implant such that the implant is secured between the fastening device and the anchor, the fastening device not extending to the intermediate region;
- wherein the implant is secured to the anchor by placing the implant over a proximal portion of the anchor between a head of the anchor and the intermediate region of the anchor, the proximal portion is devoid of external threads and has a diameter that is at least approximately the same as a diameter of external threads of the intermediate region.

* * * * *